(12) United States Patent
Hasumi et al.

(10) Patent No.: US 9,216,987 B2
(45) Date of Patent: Dec. 22, 2015

(54) CHROMAN DERIVATIVE
(71) Applicant: TMS CO., LTD., Inagi-shi, Tokyo (JP)
(72) Inventors: Keiji Hasumi, Inagi (JP); Eriko Suzuki, Fuchu (JP); Yuuichi Nishimura, Fuchu (JP); Yoshikazu Kitano, Fuchu (JP); Keiko Hasegawa, Tokyo (JP); Naoko Nishimura, Tama (JP); Kohta Tsujihara, Kawagoe (JP)
(73) Assignee: TMS CO., LTD., Tokyo (JP)
( * ) Notice: Subject to any disclaimer, the term of this patent is extended or adjusted under 35 U.S.C. 154(b) by 0 days.
(21) Appl. No.: 14/381,154
(22) PCT Filed: Mar. 1, 2013
(86) PCT No.: PCT/JP2013/055729
§ 371 (c)(1),
(2) Date: Aug. 26, 2014
(87) PCT Pub. No.: WO2013/129661
PCT Pub. Date: Sep. 6, 2013
(65) Prior Publication Data
US 2015/0025251 A1    Jan. 22, 2015
(30) Foreign Application Priority Data
Mar. 2, 2012    (JP) ................. 2012-046893
(51) Int. Cl.
*C07D 311/58* (2006.01)
*C07D 491/052* (2006.01)
*C12P 17/06* (2006.01)
(52) U.S. Cl.
CPC .......... *C07D 491/052* (2013.01); *C07D 311/58* (2013.01); *C12P 17/06* (2013.01)
(58) Field of Classification Search
None
See application file for complete search history.
(56) References Cited

FOREIGN PATENT DOCUMENTS

| EP | 2 000 540 | 10/2008 |
|---|---|---|
| JP | 2004224737 | 8/2004 |
| JP | 4313049 | 8/2009 |
| JP | 2011157293 | 8/2011 |
| WO | WO2007/111203 | 10/2007 |
| WO | WO2011/004620 | 1/2011 |

OTHER PUBLICATIONS

Shibata, Keita, et al., A novel finding of a low-molecular-weight compound, SMTP-7, having thrombolytic and anti-inflammatory effects in cerebral infarction of mine, Naunyn-Schmied Arch Pharmacol (2010) 382:245-253, Published Aug. 3, 2010, © The Author(s) 2010, pp. 245-253.
Ritsuko, Takayasu, et al., Enhancement of fibrin binding and activation of plasminogen by staplabin through induction of a conformational change in plasminogen, FEBS Letters 418 (1997) 58-62, 0014-5793/97/S17.00 © 1997 Federal of European Biochemical Socieites, pp. 58-62.
PCT/JP2013/055729, International Preliminary Report on Patentability, dated Dec. 20, 2013, 11 pages—English, 3 pages—Japanese.
PCT/JP2013/055729, Written Opinion, dated May 14, 2013, 6 pgs—Japanese; 10 pgs.—English.
PCT/JP2013/055729—Response to Written Opinion, 6 pages—Japanese.
Hu W et al., Selective Production of Staplabin and SMTPs in Cultures of Stachybotrys microspora Fed with Precursor Amines, J Antibiot., 2001, vol. 54, p. 962-966.
JP 2011-157293 A (Tokyo University of Agriculture and Technology, TMS Co., LTd.), Aug. 18, 2011, claims; fig. 1; paragraphs (0016) to (0029); examples (Family: none).
Nishimura Y et al., Pre-SMTP, a key precursor for the biosynthesis of the SMTP plasminogen modulators, J Antibiot., Jun. 2012, vol. 65, p. 483-485.
Koide, H et al., A New Series of the SMTP plasminogen modulators with a phenylamine-based side chain, J. Antibiot., 2012, 7 pages.
PCT/JP2013/055729, Notification of Receipt of Demand by Competent International Preliminary Examining Authority, dated Oct. 22, 2013, 1 page—English, 1 page—Japanese.
PCT/JP2013/055729, Amendment dated Oct. 1, 2013, 4 pgs.—English, 4 pgs.—Japnese.
Chinese Pat. Appln. Serial No. 201380010897.X, Office Action issued Jul. 10, 2015, 5 pages—English, 5 pages—Chinese.
"Synthesis of tricyclic pyrano [2,3-e] isoindolin-3-ones as the core structure of s achybotrin A, B, and C", Seiichi Inoue et al., Chem. Commun. 2006, Issue 18, pp. 1974-1976.
"Comparative study on the use of ortho-phthalaldehyde, naphthalene-2,3-dicarboxaldehyde and anthracene-2,3-dicarboxaldehyde-reagents for a-amino acids followed by the enantionmer separation of the formed isoindolin-1-one derivatives using quinine-type chiral stationary phases", Krisztina Gyimesi-Forras, et al., Journal of Chromatography A, vol. 1083, pp. 80-88.
EP 13755532.2, International Search Report mailed Oct. 7, 2015, 7 pages—English.
Staplabin, A Novel Fungal Triprenyl Phenol which Stimulates the Binding of Plasminogen of Fibrin and U937 Cells, Chikara Shinohara, et al., Journal of Antibiotics, Japan Antibiotics Research Association, Tokyo, JP, vol. 49, No. 10, Oct. 25, 1996, pp. 961-966, XP008144099, ISSN: 0021-8820.
Yuriko C. Nozawa, et al.: "Stachybotrin C and Parvisporin, novel neuritogenic compounds II. Structure determination", The Journal of antibiotics, Jan. 1, 1997, pp. 641-645, XP055213829, Retrieved from the internet: URL:https://www.jstage.jst.go.jp/article/antibiotics_1968/50/8/50 8 641/pdf (retrieved on Sep. 16, 2015).

*Primary Examiner* — Nyeemah A Grazier
(74) *Attorney, Agent, or Firm* — Andrew F. Young, Esq.; Lackenbach Siegel, LLP

(57) ABSTRACT

The invention provides a chroman derivative represented by the following Formula (I) that enables the production of an SMTP compound having a desired structure:

$$X_n-L\underset{R^2O}{\underbrace{\phantom{XXXXXXXX}}}\overset{O}{\underset{OR^1}{\underbrace{\phantom{XXXXXXXX}}}}\overset{Y^1}{\underset{Y^2}{\phantom{X}}}\quad(I)$$

wherein, in Formula (I), each of $Y^1$ and $Y^2$ independently represents a hydrogen atom, a hydroxy group, an alkoxy group, an aryloxy group, or a halogen atom; each of $R^1$ and $R^2$ independently represents a hydrogen atom, an alkyl group, an aryl group, an acyl group, an alkoxycarbonyl group, an aryloxycarbonyl group, or a carbamoyl group; L represents an aliphatic hydrocarbon group having from 4 to 10 carbon atoms; each X independently represents a hydroxy group or a carboxy group; and n represents an integer from 0 to 2.

10 Claims, No Drawings

CHROMAN DERIVATIVE

CROSS REFERENCE TO RELATED APPLICATIONS

This application claims priority from PCT Ser. No. PCT/JP2013/055729 filed Mar. 1, 2013, which in turn claims priority from JP Ser. No. 2012-046893 filed Mar. 2, 2012, the entire contents of each which are herein incorporated by reference.

TECHNICAL FIELD

The present invention relates to a chroman derivative.

BACKGROUND ART

*Stachybotrys* microspora triprenyl phenol (SMTP) compounds are a group of compounds that are produced by filamentous fungi and have a triprenyl phenol skeleton, and known to have a thrombolysis enhancing activity and an angiogenesis inhibiting activity (for example, see Japanese Patent Application Laid-Open (JP-A) No. 2004-224737, Japanese Patent No. 4313049, and International Publication No. WO 2007/111203). With regard to the thrombolysis enhancing activity, a mechanism of action has been suggested in which SMTP compounds induce a conformational change in plasminogen, and resultantly increase susceptibility of plasminogen to t-PA and enhance the binding of plasminogen to thrombi, thereby enhancing thrombolysis (for example, see FEBS Letter 1997; 418: 58-62). SMTP compounds are expected to serve as a therapeutic agent for thrombotic stroke (for example, see N. -S. Arch. Pharmacol., 382, 245-253 (2010)), a cytoprotective agent (for example, see International Publication No. WO 2011/004620), or the like.

The SMTP compounds have a geranylmethyl moiety, a tricyclic γ-lactam moiety containing a γ-lactam ring, and a side chain moiety linked to the nitrogen atom of the lactam ring. It is suggested that the activity as a plasminogen modulator depends on the structure of the side chain moiety linked to the nitrogen atom of the lactam ring, from among the moieties described above (for example, see J. Antibiot., 63, 589-593(2010)).

SUMMARY OF INVENTION

Technical Problem

Heretofore, SMTP compounds have been obtained as metabolites of filamentous fungi in the presence of an amine compound serving as a precursor of the side chain moiety linked to the nitrogen atom of the lactam ring. In such a method in which filamentous fungi are used, there are cases in which SMTP compounds having a desired structure at a side chain moiety linked to the nitrogen atom of the lactam ring are difficult to obtain.

An object of the present invention is provision of a chroman derivative that enables the production of an SMTP compound having a desired structure, and a method of producing a SMTP compound using the chroman derivative.

Solution to Problem

Specific means for achieving the object include the following aspects.

<1> A chroman derivative that is a compound represented by the following Formula (I).

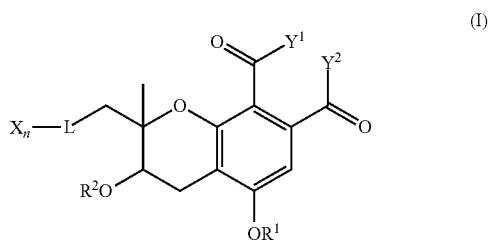

wherein, in Formula (I), each of $Y^1$ and $Y^2$ independently represents a hydrogen atom, a hydroxy group, an alkoxy group, an aryloxy group, or a halogen atom; each of $R^1$ and $R^2$ independently represents a hydrogen atom, an alkyl group, an aryl group, an acyl group, an alkoxycarbonyl group, an aryloxycarbonyl group, or a carbamoyl group; L represents an aliphatic hydrocarbon group having from 4 to 10 carbon atoms; each X independently represents a hydroxy group or a carboxy group; and n represents an integer from 0 to 2.

<2> The chroman derivative according to <1>, in which the chroman derivative is a compound represented by the following Formula (Ia).

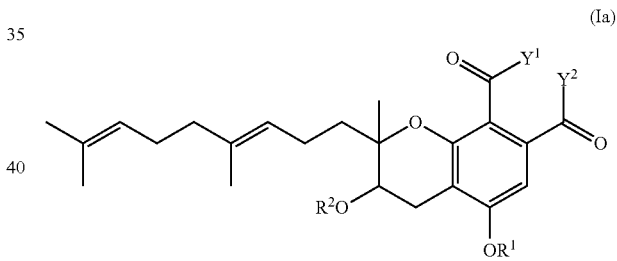

wherein, in Formula (Ia), $Y^1$, $Y^2$, $R^1$, and $R^2$ have the same definitions as $Y^1$, $Y^2$, $R^1$, and $R^2$ in Formula (I), respectively.

<3> The chroman derivative according to <1> or <2>, in which each of $Y^1$ and $Y^2$ represents a hydrogen atom.

<4> A method of producing a compound represented by the following Formula (II), the method including a step of allowing a compound represented by the following Formula (I) to react with an amine compound represented by the following Formula (III).

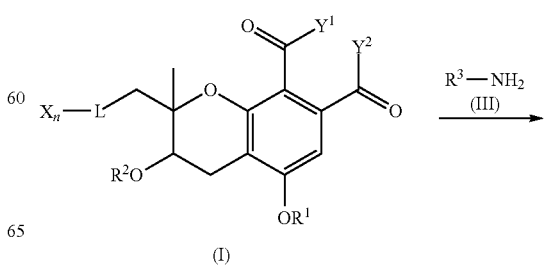

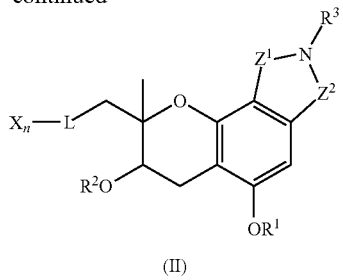

(II)

wherein, in the formulae, each of $Y^1$ and $Y^2$ independently represents a hydrogen atom, a hydroxy group, an alkoxy group, an aryloxy group, or a halogen atom; each of $R^1$ and $R^2$ independently represents a hydrogen atom, an alkyl group, an aryl group, an acyl group, an alkoxycarbonyl group, an aryloxycarbonyl group, or a carbamoyl group; L represents an aliphatic hydrocarbon group having from 4 to 10 carbon atoms; each X independently represents a hydroxy group or a carboxy group; n represents an integer from 0 to 2; each of $Z^1$ and $Z^2$ independently represents a carbonyl group or a methylene group; and $R^3$ represents a hydrogen atom, an alkyl group, an aryl group, or a heterocyclic group.

Advantageous Effects of Invention

According to the invention, a chroman derivative that enables the production of an SMTP compound having a desired structure, and a method of producing an SMTP compound using the chroman derivative can be provided.

DESCRIPTION OF EMBODIMENTS

The chroman derivative according to the invention is a compound represented by the following Formula (I). The possession of a specific structure represented by Formula (I) enables efficient production of SMTP compounds having desired structures. Among the compounds represented by Formula (I), a compound in which each of $Y^1$ and $Y^2$ represents a hydrogen atom can be found in a culture product of a filamentous fungus (such as S. microspora). Further, by allowing the compound represented by Formula (I) in which each of $Y^1$ and $Y^2$ represents a hydrogen atom to contact with an amine compound, an SMTP compound corresponding to the amine compound can be obtained non-enzymatically. Accordingly, the compound represented by Formula (I) in which each of $Y^1$ and $Y^2$ represents a hydrogen atom can be regarded as a direct intermediate in the production of an SMTP compound by a filamentous fungus.

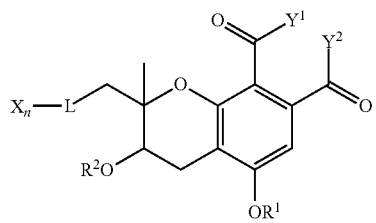

(I)

In Formula (I), each of $Y^1$ and $Y^2$ independently represents a hydrogen atom, a hydroxy group, an alkoxy group, an aryloxy group, or a halogen atom. Each of $R^1$ and $R^2$ independently represents a hydrogen atom, an alkyl group, an aryl group, an acyl group, an alkoxycarbonyl group, an aryloxycarbonyl group, or a carbamoyl group. L represents an aliphatic hydrocarbon group having from 4 to 10 carbon atoms. X represents a hydroxy group or a carboxy group. n represents an integer from 0 to 2.

Some of the compounds represented by Formula (I) have one or plural asymmetric carbon atoms or asymmetric centers in the structures thereof, and possibly have two or more optical isomers. The scope of the invention also encompasses all of individual optical isomers and any mixtures in which such optical isomers are contained at any ratios. Some of the compounds represented by Formula (I) have two or more geometric isomers due to presence of a carbon-carbon double bond in the structures thereof. The scope of the invention also encompasses any mixtures in which such geometric isomers are contained at any ratios.

Examples of the halogen atom represented by any of $Y^1$ or $Y^2$ include a fluorine atom, a chlorine atom, a bromine atom, and an iodine atom. Among these, the halogen atom is preferably a fluorine atom, a chlorine atom, or a bromine atom, and more preferably a chlorine atom or a bromine atom.

The alkyl group in the alkoxy group represented by any of $Y^1$ or $Y^2$ may be a straight chain alkyl group, a branched chain alkyl group, or a cyclic alkyl group. The carbon number of the alkyl group is not particularly limited. The alkyl group is, for example, an alkyl group having from 1 to 12 carbon atoms, preferably an alkyl group having from 1 to 8 carbon atoms, and more preferably an alkyl group having from 1 to 4 carbon atoms.

The alkyl group may have a substituent. Examples of the substituent include a hydroxy group, a halogen atom, an alkyl group, an aryl group, an alkoxy group, and an aryloxy group. The number of substituents and substitution positions thereof in the alkyl group are not particularly limited, as long as substitution is possible.

Specific examples of the alkoxy group represented by any of $Y^1$ or $Y^2$ include a methoxy group, an ethoxy group, a propoxy group, an isopropoxy group, a butoxy group, a t-butoxy group, a pentyloxy group, a hexyloxy group, a cyclohexyloxy group, an octyloxy group, an ethylhexyloxy group, a decyloxy group, and a dodecyloxy group.

The aryl group in the aryloxy group represented by any of $Y^1$ or $Y^2$ is preferably an aryl group having from 6 to 14 carbon atoms, more preferably an aryl group having from 6 to 10 carbon atoms, and still more preferably a phenyl group. The aryl group may have a substituent. Specific examples of the substituent include those mentioned as specific examples of the substituent on the alkyl group. The number of substituents and substitution positions thereof in the aryl group are not particularly limited, as long as substitution is possible. The aryl group may form a condensed ring together with an aliphatic ring.

Specific examples of the aryloxy group represented by any of $Y^1$ or $Y^2$ include a phenoxy group, a naphthyloxy group, and an anthracenyloxy group.

The alkyl group represented by any of $R^1$ or $R^2$ has the same definition and the same preferable embodiments as the alkyl group in the alkoxy group represented by $Y^1$ or $Y^2$. The aryl group represented by any of $R^1$ or $R^2$ has the same definition and the same preferable embodiments as the aryl group in the aryloxy group represented by $Y^1$ or $Y^2$.

Specific examples of the alkyl group represented by any of $R^1$ or $R^2$ include a methyl group, an ethyl group, a propyl group, an isopropyl group, a butyl group, a t-butyl group, a pentyl group, a hexyl group, a cyclohexyl group, an octyl group, an ethylhexyl group, a decyl group, and a dodecyl group. Specific examples of the alkyl group represented by any of $R^1$ or $R^2$ further include substituted alkyl groups such as a benzyl group, a phenethyl group, a methoxymethyl group, and a methoxyethoxymethyl group.

Specific examples of the aryl group represented by any of $R^1$ or $R^2$ include a phenyl group, a naphthyl group, and an anthracenyl group.

The acyl group represented by any of $R^1$ or $R^2$ may be an alkylcarbonyl group or an arylcarbonyl group. The alkyl group in the alkylcarbonyl group has the same definition and the same preferable embodiments as the alkyl group in the alkoxy group represented by $Y^1$ or $Y^2$. The aryl group in the arylcarbonyl group has the same definition and the same preferable embodiments as the aryl group in the aryloxy group represented by $Y^1$ or $Y^2$.

Specific examples of the acyl group represented by any of $R^1$ or $R^2$ include an acetyl group, a propionyl group, a butanoyl group, and a benzoyl group.

The alkyl group in the alkyloxycarbonyl group represented by any of $R^1$ or $R^2$ has the same definition and the same preferable embodiments as the alkyl group in the alkoxy group represented by $Y^1$ or $Y^2$. The aryl group in the aryloxycarbonyl group represented by any of $R^1$ or $R^2$ has the same definition and the same preferable embodiments as the aryl group in the aryloxy group represented by $Y^1$ or $Y^2$.

Specific examples of the alkyloxycarbonyl group represented by any of $R^1$ or $R^2$ include a methoxycarbonyl group, an ethoxycarbonyl group, a propyloxycarbonyl group, and a t-butyloxycarbonyl group. Specific examples of the aryloxycarbonyl group include a phenoxycarbonyl group.

The carbamoyl group represented by any of $R^1$ or $R^2$ may have an alkyl group or an aryl group on the nitrogen atom thereof. In a case in which the carbamoyl group has an alkyl group or an aryl group on the nitrogen atom thereof, the alkyl group has the same definition and the same preferable embodiments as the alkyl group in the alkoxy group represented by $Y^1$ or $Y^2$, and the aryl group has the same definition and the same preferable embodiments as the aryl group in the aryloxy group represented by $Y^1$ or $Y^2$.

Specific examples of the carbamoyl group represented by any of $R^1$ or $R^2$ include a carbamoyl group, a methylcarbamoyl group, an ethylcarbamoyl group, a dimethylcarbamoyl group, a diethylcarbamoyl group, and a phenylcarbamoyl group.

In Formula (I), it is preferable that each of $Y^1$ and $Y^2$ independently represents a hydrogen atom or a hydroxy group, it is more preferable that each of $Y^1$ and $Y^2$ represents a hydrogen atom or a hydroxy group, and it is still more preferable that each of $Y^1$ and $Y^2$ represents a hydrogen atom. It is preferable that each of $R^1$ and $R^2$ independently represents a hydrogen atom, an alkyl group, an aryl group, or an acyl group, it is more preferable that each of $R^1$ and $R^2$ independently represents a hydrogen atom, an alkyl group, or an acyl group, and it is still more preferable that each of $R^1$ and $R^2$ represents a hydrogen atom.

The aliphatic hydrocarbon group having from 4 to 10 carbon atoms represented by L may have a straight chain, branched chain, or cyclic aliphatic hydrocarbon group. The aliphatic hydrocarbon group may have an unsaturated bond. The aliphatic hydrocarbon group is preferably a straight chain or branched chain aliphatic hydrocarbon group that may have an unsaturated bond.

Specific examples of a group represented by -L-$X_n$ in Formula (I) include a group represented by the following Formula (L0) and a group represented by any of the following Formulae (L1) to (L4).

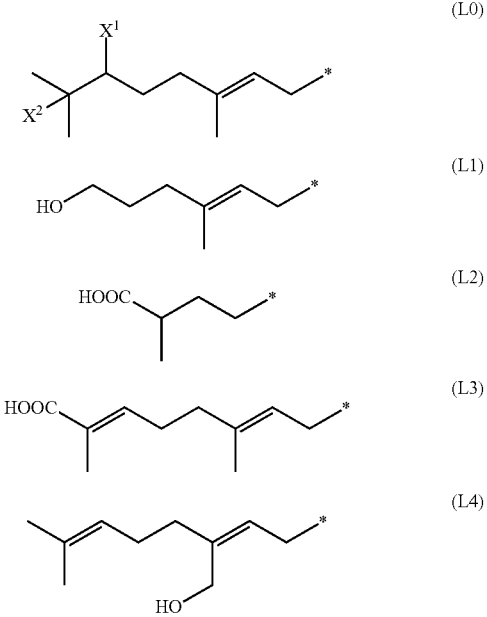

In Formula (L0), each of $X^1$ and $X^2$ independently represents a hydrogen atom or a hydroxy group, or $X^1$ and $X^2$ are linked to each other to form a single bond. Here, "*" in the above formulae indicates a linking position.

The group represented by -L-$X_n$ in Formula (I) is preferably a group represented by Formula (L0) or a group represented by any of Formulae (L1) to (L4), more preferably a group represented by Formula (L0), and still more preferably a group represented by Formula (L0) in which $X^1$ and $X^2$ are linked to each other to form a single bond. That is, the compound represented by Formula (I) is preferably a compound represented by the following Formula (Ia).

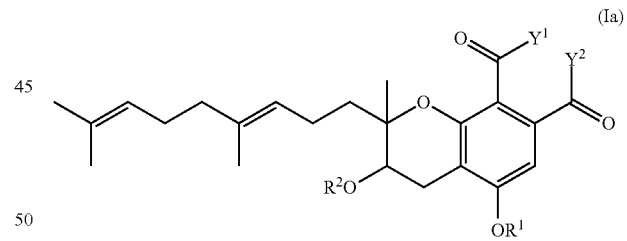

In Formula (Ia), $Y^1$, $Y^2$, $R^1$, and $R^2$ have the same definition as $Y^1$, $Y^2$, $R^1$, and $R^2$ in Formula (I), respectively. In Formula (Ia), each of $Y^1$ and $Y^2$ represents preferably a hydrogen atom or a hydroxy group, and more preferably a hydrogen atom. It is preferable that each of $R^1$ and $R^2$ independently represents a hydrogen atom, an alkyl group, an aryl group, or an acyl group, it is more preferable that each of $R^1$ and $R^2$ independently represents a hydrogen atom or an alkyl group, and it is still more preferable that each of $R^1$ and $R^2$ represents a hydrogen atom.

Specific examples of the compound represented by Formula (I) are shown below, but the invention is not limited thereto.

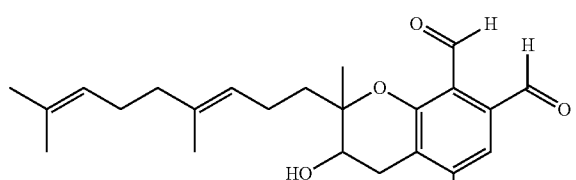
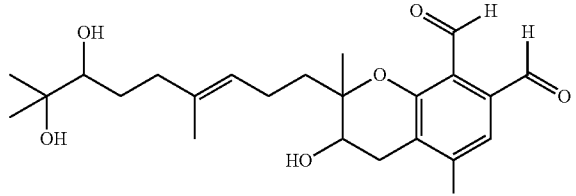
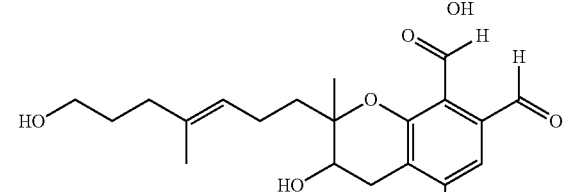
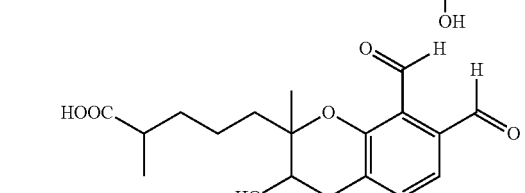
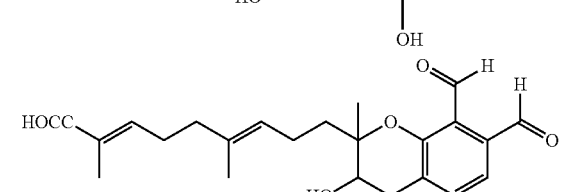
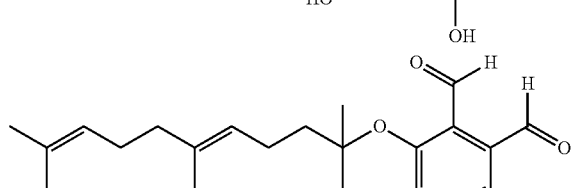
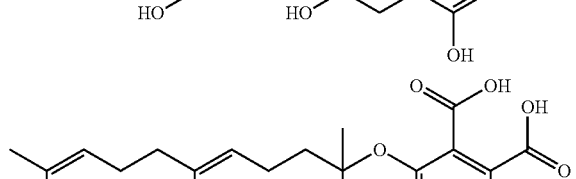
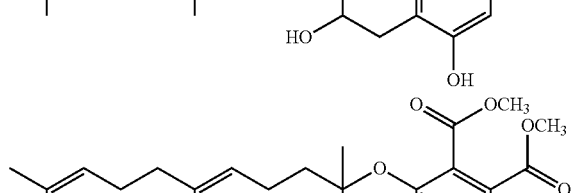
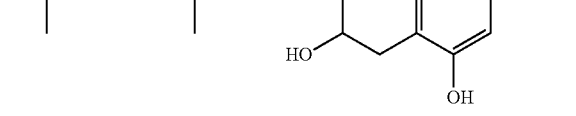
-continued
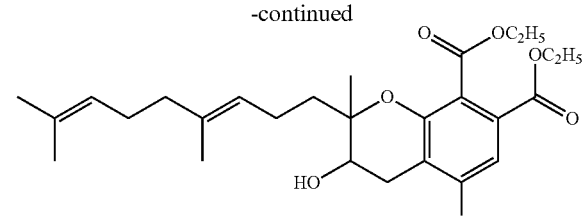
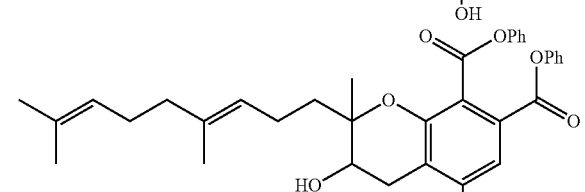
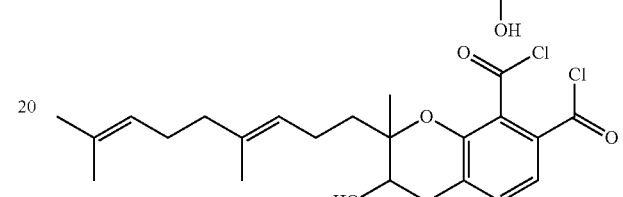
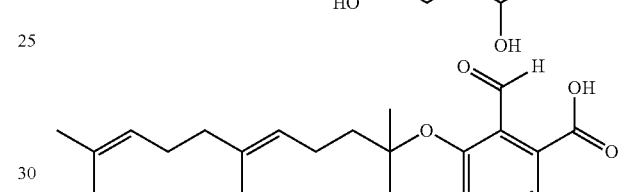
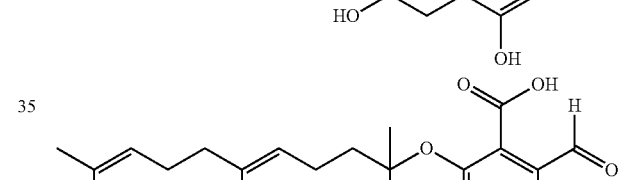
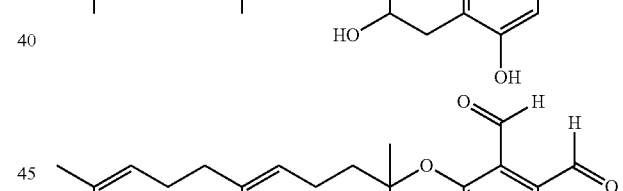
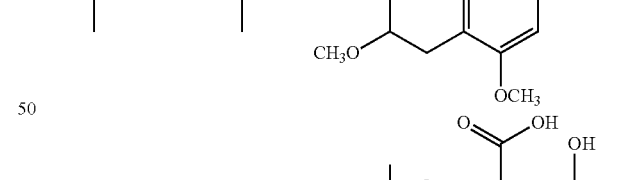
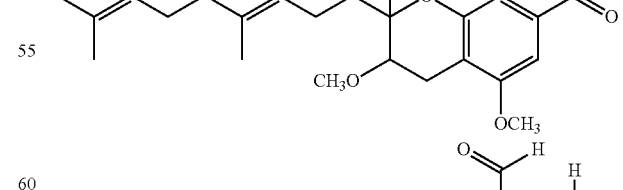
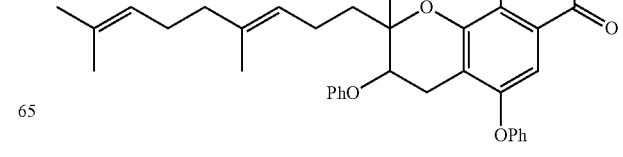

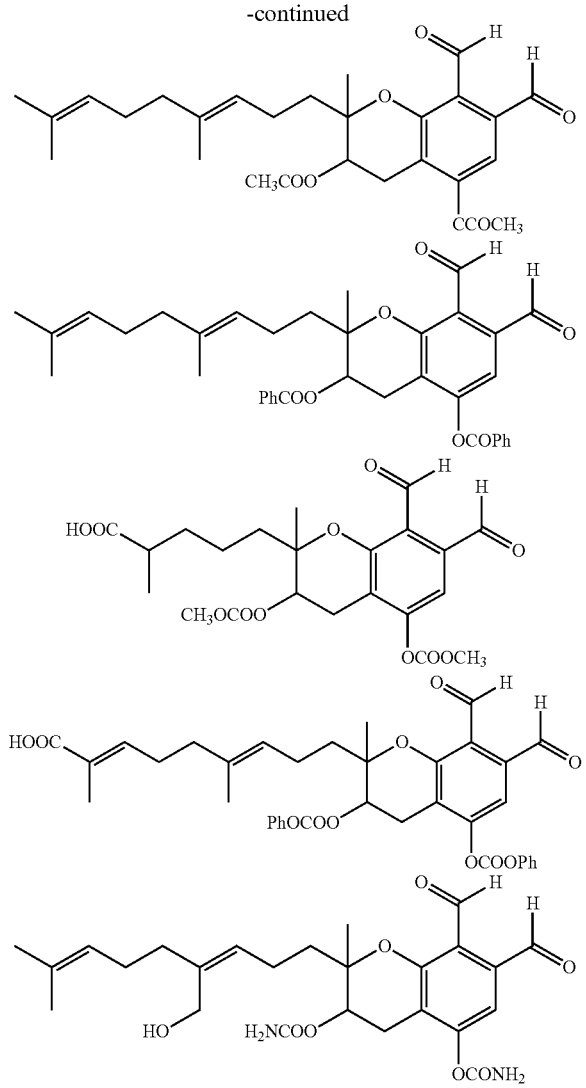

The compound represented by Formula (I) can be synthesized by an ordinarily employed synthesis method. Alternatively, the compound represented by Formula (I) can be obtained from a culture product of a filamentous fungus. More specifically, a compound represented by Formula (Ia) in which each of $Y^1$, $Y^2$, $R^1$, and $R^2$ represents a hydrogen atom (hereinafter sometimes referred to as "Pre-SMTP") can be obtained by performing a purification process, such as solvent extraction, silica-gel column chromatography, or reverse-phase HPLC, using a culture product of a filamentous fungus obtained through cultivation with a reduced amine compound content.

In the case of obtaining a compound represented by Formula (I) (preferably Pre-SMTP) from a cultured product of a filamentous fungus, the filamentous fungus to be used is selected from filamentous fungi belonging to the genus Stachybotrys. A preferable filamentous fungus belonging to the genus *Stachybotrys* is, for example, *Stachybotrys microspore*, and *S. microspore* strain IFO30018 is more preferable.

In regard to methods of culturing a filamentous fungus, the disclosure of International Publication No. WO 2007/111203, for example, may be referenced. The culture medium for culturing a filamentous fungus is not particularly limited, and may be appropriately selected from ordinarily employed culture media. For example, a medium containing a sugar, a yeast extract, an inorganic salt, and the like may be used as the culture medium for culturing a filamentous fungus. The pH of the culture medium may be, for example, from 3 to 9, and preferably from 5 to 6. The culture medium preferably has a suppressed content of amine compound in the culture medium. The content of amine compound in the culture medium is preferably 0.5% by mass or less. From the viewpoints of the growth of fungi, yield, and production selectivity, the content of amine compound in the culture medium is preferably from 0.01% by mass to 0.5% by mass, and more preferably from 0.1% by mass to 0.3% by mass. The culture conditions may be appropriately selected in accordance with, for example, the culture scale. For example, the culture temperature may be from 4° C. to 50° C., preferably from 15° C. to 37° C., more preferably from 20° C. to 30° C., and still more preferably room temperature (25° C.). The culture time is form 1 day to 8 days, and, from the viewpoint of yield, preferably 3 days to 6 days.

In a case in which a filamentous fungus is cultured using a liquid medium, it is preferable to perform fermenter culture or shaking culture The conditions for shaking culture may be appropriately selected in accordance with, for example, the culture scale. For example, in the case of a rotary shaker TB-25S (shaking amplitude of 70 mm) manufactured by Takasaki Sci. Instru. Corp., assuming that the medium volume is 100 ml in a 500 mL-volume flask, shaking culture may be performed at a rotation speed of from 30 rpm ($min^{-1}$) to 240 rpm ($min^{-1}$), preferably from 160 rpm ($min^{-1}$) to 200 rpm ($min^{-1}$).

Examples of methods of obtaining the compound represented by Formula (I) from the culture product using solvent extraction include a method of centrifuging the culture product and recovering cells of the filamentous fungus, and then adding a solvent thereto and performing ultrasonication. The solvent may be selected, without particular limitation, from solvents capable of dissolving the compound represented by Formula (I). Examples of such solvents include: nitrile solvents such as acetonitrile or propionitrile; and ketone solvents such as acetone or methyl ethyl ketone. Among these, in terms of the extraction efficiency, it is preferable to use at least one selected from the group consisting of nitrile solvents and ketone solvents.

The solvent-extracted compound represented by Formula (I) (preferably Pre-SMTP) may be subjected to purification treatment such as silica-gel column chromatography or reverse-phase HPLC. Methods for the purification treatment may be selected, as appropriate, from ordinarily employed purification methods.

Among the compounds represented by Formula (I), compounds other than the compound in which each of $Y^1$ and $Y^2$ represents a hydrogen atom may be obtained, for example, by a synthesis method ordinarily employed for Pre-SMTP. More specifically, a compound represented by Formula (I) in which at least one of $Y^1$ or $Y^2$ represents a hydroxy group can be obtained by oxidizing an aldehyde group or aldehyde groups of Pre-SMTP. The conditions for the oxidization of the aldehyde group(s) are not particularly limited, and may be appropriately selected from ordinarily employed oxidization methods. Furthermore, performing an alkyl esterification reaction, an aryl esterification reaction, or a halogenation reaction on the compound in which at least one of $Y^1$ or $Y^2$ represents a hydroxy group enables obtainment of a compound in which at least one of $Y^1$ or $Y^2$ represents an alkyloxy group, an aryloxy group, or a halogen atom, respectively. The conditions for these reactions are not particularly limited, and may be appropriately selected from ordinarily employed conditions for synthesis reactions.

In the case of at least one of $R^1$ or $R^2$ in the compound represented by Formula (I) represents a hydrogen atom, the corresponding hydroxy group can be converted into an alkyloxy group, an aryloxy group, an acyloxy group, an alkoxycarbonyloxy group, an aryloxycarbonyloxy group, or a carbamoyloxy group by ordinarily employed synthesis methods.

The compound represented by Formula (I) can be used for the production of various SMTP compounds. That is, a production method of a compound represented by Formula (II) according to the invention includes a condensation process of allowing the compound represented by the following Formula (I) and an amine compound represented by the following Formula (III) to react with each other. The production method may further include additional processes such as a purification process, if necessary.

Using the compound represented by Formula (I) as a precursor, SMTP compounds represented by Formula (II) having desired structures can be produced efficiently. Furthermore, since SMTP compounds can be produced without relying on filamentous fungi, SMTP compounds that are difficult to produce by production methods using filamentous fungi can be produced in a simple and easy manner.

That is, another aspect of the invention relates to use of a compound represented by Formula (I) in the production of a compound represented by Formula (II).

tively. It is preferable that each of $Z^1$ and $Z^2$ represents a carbonyl group, or that one of $Z^1$ or $Z^2$ represents a carbonyl group and the other represents a methylene group. It is more preferable that one of $Z^1$ or $Z^2$ represents a carbonyl group and the other represents a methylene group. It is still more preferable that $Z^1$ represents a methylene group and $Z^2$ represents a carbonyl group.

$R^3$ represents a hydrogen atom, an alkyl group, an aryl group, or a heterocyclic group. The alkyl group, the aryl group, and the heterocyclic group that $R^3$ may represent may be freely selected, without particularly limitation, from those capable of forming an amino compound. The alkyl group, the aryl group, and the heterocyclic group that $R^3$ may represent may have a substituent. Examples of the substituent in the alkyl group, the aryl group, and the heterocyclic group that $R^3$ may represent include an alkyl group, an alkoxy group, an aryl group, an aryloxy group, a carboxy group, a sulfonic acid group, an amino group, a hydroxy group, an amide group, an sulfonamide group, and a halogen atom. These substituents may themselves have a further substituent, if possible, and examples of the further substituent in the case of substitution on the substituents described above are the same as the substituents described above.

Specific examples of the compound represented by Formula (II) include the SMTP compounds described in International Publication No. WO 2011/004620 and compounds in which $R^3$ represents any of the following chemical formulae. Here, "*" in the formulae indicates a linking position.

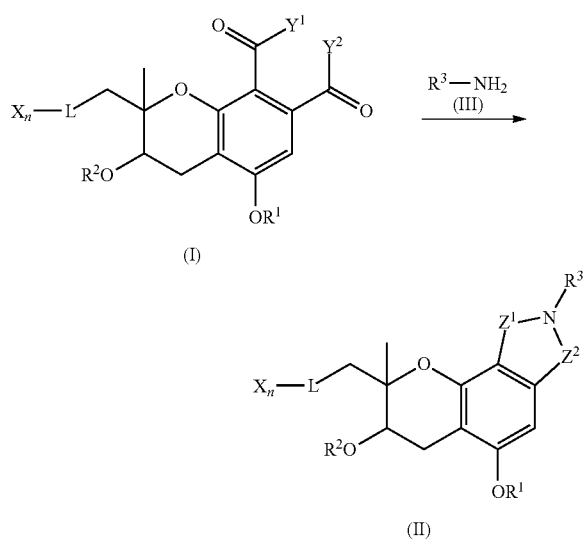

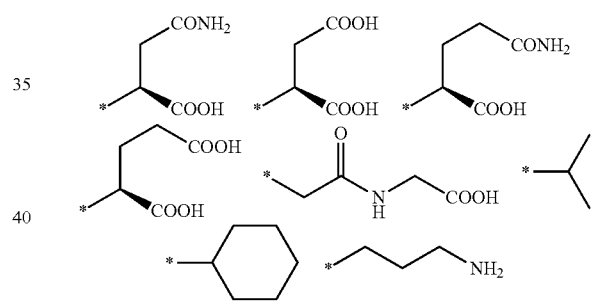

wherein, in the formulae, each of $Y^1$ and $Y^2$ independently represents a hydrogen atom, a hydroxy group, an alkoxy group, an aryloxy group, or a halogen atom. Each of $R^1$ and $R^2$ independently represents a hydrogen atom, an alkyl group, an aryl group, an acyl group, an alkoxycarbonyl group, an aryloxycarbonyl group, or a carbamoyl group. L represents an aliphatic hydrocarbon group having from 4 to 10 carbon atoms. Each X independently represents a hydroxy group or a carboxy group, and n represents an integer from 0 to 2. Each of $Z^1$ and $Z^2$ independently represents a carbonyl group or a methylene group. $R^3$ represents a hydrogen atom, an alkyl group, an aryl group, or a heterocyclic group.

$Y^1$, $Y^2$, $R^1$, $R^2$, L, X, and n in the formulae have the same definitions and the same preferable embodiments as $Y^1$, $Y^2$, $R^1$, $R^2$, L, X, and n in Formula (I) described above, respec- In the condensation process, the conditions for reacting the compound represented by Formula (I) and the amine compound represented by Formula (III) are not particularly limited, and may be appropriately selected from ordinarily employed reaction conditions. For example, the condition for reacting a compound represented by Formula (I) in which each of $Y^1$ and $Y^2$ represents a hydrogen atom and the amine compound represented by Formula (III) may be a neutral condition or an acidic condition. The reaction may be conducted in the presence of a solvent or in the absence of a solvent. The reaction temperature and the reaction time may be appropriately selected in accordance with the reactivity between the compound represented by Formula (I) and the amine compound represented by Formula (III).

Reacting the compound represented by Formula (I) in which each of $Y^1$ and $Y^2$ represents a hydrogen atom and the amine compound represented by Formula (III) enables efficient production of compounds represented by the following Formula (IIa) and compounds represented by the following Formula (IIb). In the following formulae, $R^1$ to $R^3$, L, X and n has the same definitions and the same preferable embodiments as those described above.

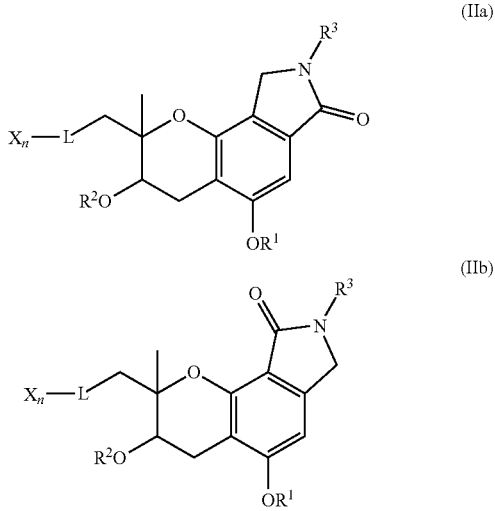

Reacting the compound represented by Formula (I) in which each of $Y^1$ and $Y^2$ represents a hydroxy group, an alkoxy group, an aryloxy group, or a halogen atom and the amine compound represented by Formula (III) enables efficient production of compounds represented by the following Formula (IIc). In the following formula, $R^1$ to $R^3$, L, X and n has the same definitions and the same preferable embodiments as those described above.

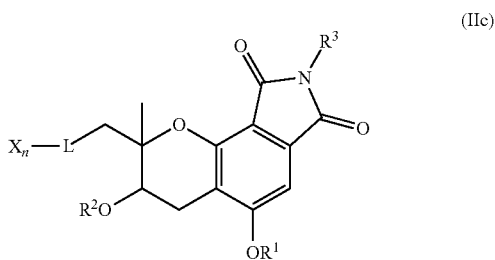

For example, reaction conditions ordinarily employed for imidization reactions may be applied as the conditions for the reaction between the compound represented by Formula (I) in which each of $Y^1$ and $Y^2$ represents a hydroxy group, an alkoxy group, an aryloxy group, or a halogen atom and the amine compound represented by Formula (III). The imidization reaction may be conducted in the presence of a solvent or in the absence of a solvent. If necessary, a reactive catalyst such as an acid or a salt may be used.

The ratio of the compound represented by Formula (I) and the amine compound represented by Formula (III) to be used in the condensation process is not particularly limited, as long as the desired compound represented by Formula (II) can be obtained. For example, the ratio of the compound represented by Formula (III) to the compound represented by Formula (I) is preferably 0.8 or more, more preferably 1.0 or more, and still more preferably from 1.0 to 3.0.

In a case in which the compound represented by Formula (I) and the amine compound represented by Formula (III) are reacted in the presence of a solvent, the solvent is not particularly limited as long as it can dissolve at least a part of the amount of the compound represented by Formula (I) and at least a part of the amount of the amine compound represented by Formula (III). Examples of the solvent include: water; alcohol solvents such as methanol and ethanol; ketone solvents such as acetone and methyl ethyl ketone; ester solvents such as ethyl acetate; ether solvents such as diethyl ether, isopropyl ether, and tetrahydrofuran; and aprotic polar solvents such as dimethylformaldehyde, dimethylacetoamide, and dimethylsulfoxide. The above-described amine compound is also usable as a solvent. These solvents may be used singly, or in combination of two of more thereof.

The reaction temperature and the reaction time in the condensation process may be appropriately selected in accordance with the reactivity of the compound represented by Formula (I) and the amine compound represented by Formula (III), and for example, a reaction temperature of from −20° C. to 200° C. and a reaction time of from 10 minutes to 6 hours may be adopted.

The method of producing a compound represented by Formula (II) may further include a purification process. The purification process is not particularly limited, as long as it is able to extract the compound represented by Formula (II) from the reaction products of the compound represented by Formula (I) and the compound represented by Formula (III), and the purification process may be appropriately selected from ordinarily employed purification methods. Specific examples of the purification method include solvent extraction, recrystallization, distillation, column chromatography, and reverse-phase HPLC.

EXAMPLES

Hereinafter, the invention is described more specifically with reference to examples, but the invention is not limited to these examples. Here, "%" is based on mass unless otherwise specified.

Example 1

Preparation of Pre-SMTP

*Stachybotrys* microspore strain IFO30018 (NBRC30018) was purchased from Institute for Fermentation, Osaka.

0.5% w/v of peptone, 0.3% w/v of yeast extract, and 0.1% w/v of $MgSO_4.7H_2O$ were dissolved in water, and the pH of the resultant was adjusted to 7.0, thereby preparing water for rehydration.

5% w/v of oatmeal and 2% w/v of agar were dissolved in water, thereby preparing an oatmeal agar.

4% w/v of glucose, 0.5% w/v of soybean meal, 0.3% of w/v polypeptone, 0.3% w/v of yeast extract, and 0.01% v/v of antifoaming agent (CB442, manufactured by NOF corporation) were dissolved in water, and the pH of the resultant was adjusted to 5.8, thereby preparing a preculture medium.

5% w/v of sucrose, 0.1% w/v of yeast extract, 0.7% w/v of $KNO_3$, 1.5% w/v of $K_2HPO_4$, 0.05% w/v of $MgSO_4.7H_2O$, 0.05% w/v of KCl, 0.00025% w/v of $CoCl_2.6H_2O$, 0.0015% w/v of $FeSO_4.7H_2O$, 0.00065% w/v of $CaCl_2.2H_2O$, and 0.01% v/v of antifoaming agent (CB442, manufactured by NOF corporation) were dissolved in water, and the pH of the resultant was adjusted to 5.8, thereby preparing a main culture medium.

To L-dried cells of *Stachybotrys* microspore IFO30018, 250 μL of the water for rehydration was added to suspend. 25 μL of the suspension was streaked onto an oatmeal agar slant, and then subjected to static culture at 25° C. for 5 days or more. Subsequently, the cultured cells were inoculated into 100 mL (per conical flask) of the preculture medium and subjected to shaking culture (180 rpm, 25° C.) for 4 days, thereby obtaining a preculture solution. 5 mL of the preculture solution was then inoculated into 100 mL of the main culture medium and subjected to a shaking culture (180 rpm, 25° C.) for 5 days, thereby obtaining a culture solution.

1.5 L of the obtained culture solution was centrifuged (from 2,500 to 3,000×g, 20 minutes), and the supernatant was discarded. 300 mL of acetonitrile was added to the remaining cells, and the mixture was subjected to sonication. The extract solution was then collected by suction filtration. Thereafter, the cells, which were filtration residues, were collected by scraping from the filter, 150 mL of acetonitrile was added to the cells, and the cells were subjected to sonication. The extract solution was then collected by suction filtration. In this manner, a total of 450 mL extract solution (hereinafter sometimes referred to as "Pre-SMTP extract solution") was collected.

The acetonitrile was distilled away from the obtained extract, and 4.6 g of the resultant residue was subjected to silica-gel column chromatography. Specifically, the column was washed with 1 L of n-hexane, and then elution was performed with n-hexane and ethyl acetate (in a ratio of 4:1, which was then changed to 3:2, in an amount of 4.6 L in each of the elution steps). The fraction eluted with n-hexane and ethyl acetate in a ratio of 3:2 was collected, and the solvent was distilled away, thereby obtaining a yellow oily residue. This residue was dissolved in acetonitrile, treated with a LICHROLUT RP-18 (manufactured by Merck & CO. Inc.), and then purified by HPLC fractionation (flow rate: 25 mL/min, column temperature: 40° C.) using an ODS column (INERTSIL PREP-ODS, 30mm-diameter×250 mm; manufactured by GL Sciences Inc). Using (A) 0.1% aqueous formic acid solution and (B) acetonitrile as the mobile phase, the elution was performed with a linear gradient of (B) acetonitrile increasing from 50% by volume to 100% by volume over 30 minutes. The fraction containing the target substance was concentrated and dried, thereby obtaining 24.8 mg of Pre-SMTP represented by the following formula. Here, the indexes in the following chemical formulae indicate the position numbers of the carbon.

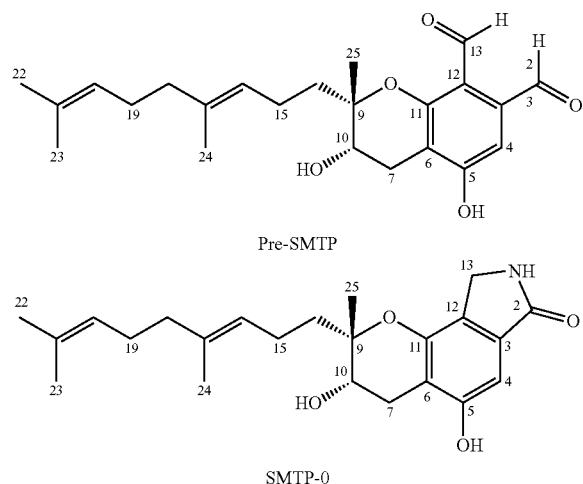

Pre-SMTP

SMTP-0

Analysis of physicochemical feature and structure of Pre-SMTP

Ultraviolet spectrum (UV spectrum) was measured with a model 320 spectrometer (manufactured by Hitachi High-Technologies Corporation) using acetonitrile as a solvent.

Infrared spectrum (IR spectrum) was measured with a JIR-WINSPEC spectrometer (manufactured by JEOL Ltd.) using the NaCl method.

The mass spectrum (MALDI-TOF-MS spectrum) was measured with a VOYAGER DE STR spectrometer (manufactured by Applied Biosystems) using α-cyano-4-hydroxycinnamic acid as a matrix.

Nuclear magnetic resonance spectrum (NMR spectrum) was measured with an ALPHA-600 spectrometer (manufactured by JEOL Ltd.) using acetone-$d_6$ (manufactured by Acros Organics). In addition to the $^1$H spectrum and $^{13}$C spectrum, which are usually measured, HMQC (Hetero-nuclear Multiple Quantum Coherence) spectrum and HMBC (Hetero-nuclear Multiple-Bond Connectivity) spectrum were also measured as $^1$H-$^{13}$C correlation NMR spectra. A carbonyl carbon ($^{13}$C): 206.1 ppm, a methyl carbon ($^{13}$C): 29.8 ppm, and a methyl proton ($^1$H): 2.04 ppm of acetone-$d_6$ were used as internal standards.

Specific rotation was measured with a model DIP-360 (manufactured by JASCO Corporation.) using acetonitrile as a solvent.

The results are shown in Tables 1 and 2. For the purpose of reference, the NMR measurement results of SMRP-0, a well-known SMTP compound, are also indicated in Table 2.

TABLE 1

| | |
|---|---|
| Appearance | Pale yellow oil |
| Molecular formula | $C_{23}H_{30}O_5$ |
| MALDI-TOF-MS (m/z) | |
| Found (M − H)$^-$: | 385.2021 |
| Calculated: | 385.2014 for $C_{23}H_{29}O_5$ |
| UV$\lambda_{max}$ nm (ε) $CH_3CN$ | 240 (16,387), 258 (12,367, sh), 295 (6,261) |
| IR $\nu_{max}$ (neat) cm$^{-1}$ | 3427, 2970, 1684, 1583, 1500, 1435, 1381, 1317, 1234, 1088 |
| Specific rotation $[\alpha]_D^{25}$ | −35.8° (c 1.0, $CH_3CN$) |

TABLE 2

| | Pre-SMTP | | SMTP-0 | |
|---|---|---|---|---|
| No. | $\delta_C$ | $\delta_H$ | $\delta_C$ | $\delta_H$ |
| 2 | 190.06 | 10.37 (1H, s) | 170.24 | |
| 3 | 139.33 | | 131.78 | |
| 4 | 106.66 | 6.85 (1H, s) | 99.44 | 6.62 (1H, s) |
| 5 | 161.96 | | 155.93 | |
| 6 | 114.15 | | 111.29 | |
| 7 | 27.38 | 3.02 (1H, dd, J = 5.7, 17.7) 2.67 (1H, dd, J = 7.2, 17.4) | 26.59 | 2.82 (1H, dd, J = 5.5, 17.4) 2.45 (1H, dd, J = 7.7, 17.6) |
| 8 | 66.89 | 4.00 (1H, dd, J = 5.4, 7.8) | 66.01 | 3.73 (1H, t, J = 6.4) |
| 9 | 81.46 | | 78.52 | |
| 11 | 159.17 | | 148.45 | |
| 12 | 118.32 | | 121.61 | |
| 13 | 193.06 | 10.46 (1H, s) | 41.95 | 4.09 (1H, d, J = 17.2) 4.05 (1H, d, J = 16.9) |
| 14 | 38.41 | 1.80 (2H, m) | 37.14 | 1.59 (2H, m) |
| 15 | 22.34 | 2.25 (2H, m) | 20.93 | 2.10 (2H, m) |
| 16 | 125.15 | 5.18 (1H, m) | 124.16 | 5.11 (1H, t, J = 6.6) |
| 17 | 135.83 | | 134.18 | |
| 18 | 40.38 | 1.97 (2H, t, J = 7.2) | 39.04 | 1.91 (2H, m) |
| 19 | 27.20 | 2.06 (2H, m) | 26.06 | 1.99 (2H, m) |
| 20 | 125.05 | 5.08 (1H, m) | 123.98 | 5.04 (1H, t, J = 7.1) |
| 21 | 131.67 | | 130.52 | |
| 22 | 25.78 | 1.63 (3H, s) | 25.27 | 1.61 (3H, s) |
| 23 | 17.68 | 1.56 (3H, s) | 17.36 | 1.53 (3H, s) |
| 24 | 15.99 | 1.61 (3H, s) | 15.48 | 1.54 (3H, s) |
| 25 | 18.38 | 1.36 (3H, s) | 17.95 | 1.15 (3H, s) |

As a result of the HNBC measurement, as indicated in the following chemical formula, correlation peaks were observed, for example, between the hydrogen atom bonded to the carbonyl carbon at 2-position and the carbon atom at 3-position, and between the hydrogen atom bonded to the carbonyl carbon at 13-position and the carbon atom at 12-position. Here, the arrow shown in the chemical formula indicates that the correlation peaks were observed between the hydrogen atom positioned at the starting point of the arrow and the carbon atom positioned at the end point of the arrow. In this manner, the structure of Pre-SMTP was confirmed.

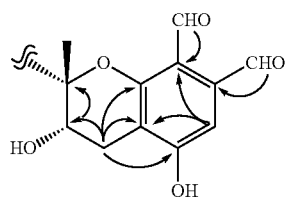

Example 2

To 200 mL of the obtained Pre-SMTP extract solution, 200 mL of an aqueous solution containing an amine compound noted in Table 3 at an concentration of 11.5 mg/mL and 4.0 mL of acetic acid were added, and the mixture was allowed to stand still for 1 hour at room temperature. After the solvent was distilled away, the obtained residue was dissolved in acetone and centrifuged (from 2,500 to 3,000×g, 20 minutes). The supernatant was collected, concentrated, and dried. The obtained dried matter was dissolved in methanol and centrifuged (from 2,500 to 3,000×g, 20 minutes). The supernatant was collected and treated with a pre-column (DISCOVERY DSC-18 1 mL; manufactured by SUPELCO), and then purified by HPLC fractionation (flow rate: 25 mL/min, column temperature: 40° C.) using an ODS column (INERTSIL PREP-ODS, 30 mm-diameter×250 mm; manufactured by GL Sciences Inc). Specifically, using (A) 0.1% aqueous formic acid solution and (B) acetonitrile as the mobile phase, elution was performed under the conditions indicated in Table 3 ("%" in Table 3 is based on volume). The obtained fraction was concentrated and dried, and washing was performed by adding hexane. The resultant was centrifuged (from 2,500 to 3,000×g, 20 minutes), and the supernatant was discarded. The precipitate was collected, dissolved in methanol, and filtered through absorbent cotton. The filtered substance was concentrated and dried using nitrogen gas, thereby obtaining a target SMTP compound as a dried material. The structure of the obtained SMTP compound is shown in Table 4. In Table 4, "*" indicates a linking position in $R^3$.

TABLE 3

| Compound number | Amine compound | Yield (mg/L (Broth)) | Retention time (min.) | HPLC condition |
|---|---|---|---|---|
| SMTP-52 | L-Asparagine | 34.4 | 16.4 | 45% acetonitrile |
| SMTP-53 | L-Aspartic acid | 23.5 | 16.2 | 45% acetonitrile |
| SMTP-54 | L-Glutamine | 25.4 | 16.1 | 45% acetonitrile |
| SMTP-55 | L-Glutamic acid | 21.1 | 14.1 | 50% acetonitrile |
| SMTP-56 | Glycylglycine | 16.5 | 14.2 | 50% acetonitrile |
| SMTP-57 | Isopropylamine | 31.8 | 13.1 | 75% acetonitrile |
| SMTP-58 | Cyclohexylamine | 29.0 | 16.6 | 80% acetonitrile |
| SMTP-59 | 1,3-Diaminopropane | 29.4 | 15.5 | 40% acetonitrile |

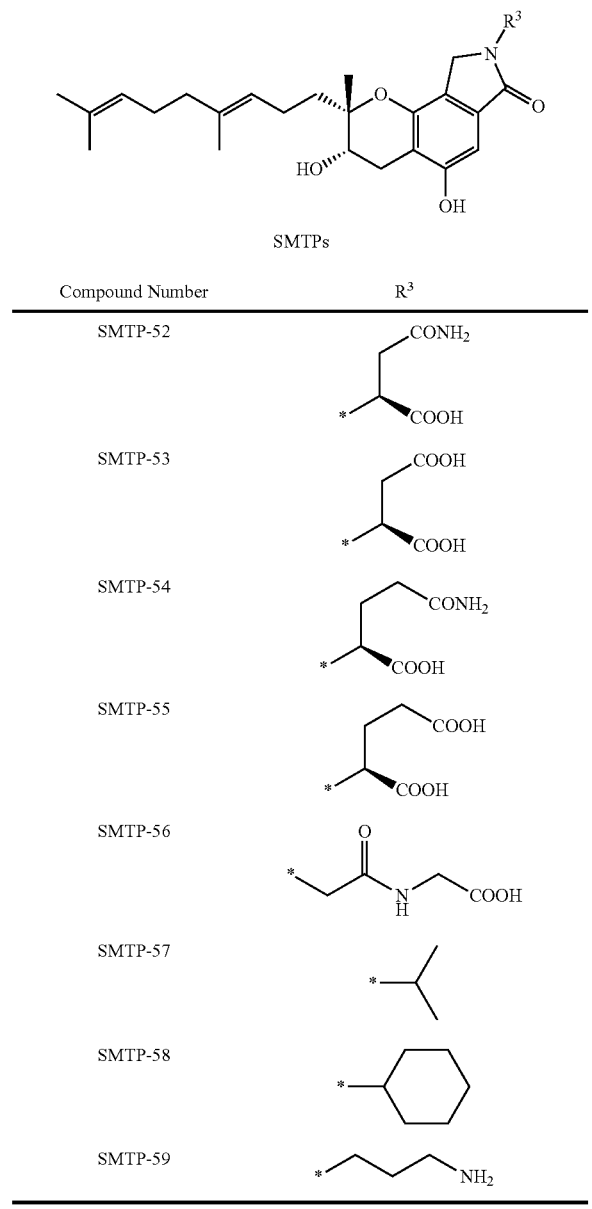

Example 3

Pre-SMTP was dissolved in acetone to prepare a 100 μg/mL pre-SMTP solution. The obtained Pre-SMTP solution was mixed with an equal amount of 1.9 mg/mL aqueous ammonium acetate solution, and the resultant mixture was left to stand for 60 minutes at room temperature. The supernatant of the reaction mixture was analyzed using reverse-phase HPLC, and it was confirmed that an SMTP compound corresponding to the use of the ammonia as the amine compound (SMTP-0, in which $R^3$ in Table 4 is a hydrogen atom) was produced.

Further, a reaction was conducted in the same manner as that described above, except that a 5 mg/mL aqueous L-phenylalanine solution or a 5 mg/mL aqueous L-tryptophan solution was used instead of the ammonium acetate. Further, it was confirmed that an SMTP compound corresponding to the use of L-phenylalanine as the amine compound (SMTP-4) and an SMTP compound corresponding to the use of L-tryptophan as the amine compound (SMTP-6), respectively, were produced in the respective cases.

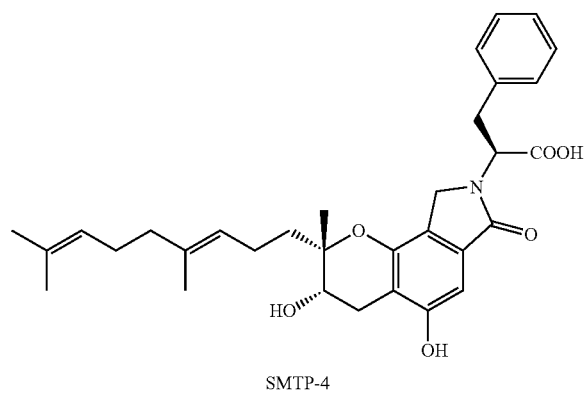

SMTP-4

SMTP-6

Example 4

The reaction was conducted in the same manner as in Example 3, except that 20 mM phosphate buffer (pH 7.4, containing 0.2% w/v Tween 80 and 2% v/v acetone) was used instead of the acetone, and it was confirmed that a SMTP compound corresponding to the amine compound was produced, similar to Example 3.

These results demonstrate that, by allowing the compound represented by Formula (I) to react with an amine compound, a compound represented by Formula (II) and having a desired structure can be produced in a simple and easy manner.

The disclosure of Japanese Patent Application No. 2012-046893 is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A chroman derivative that is a compound represented by the following Formula (Ia):

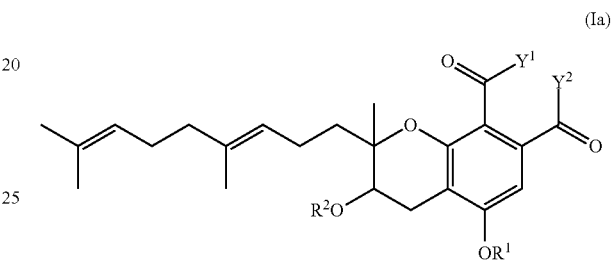

(Ia)

wherein, in Formula (Ia), each of $Y^1$ and $Y^2$ independently represents a hydrogen atom, a hydroxy group, an alkoxy group, an aryloxy group, or a halogen atom; each of $R^1$ and $R^2$ independently represents a hydrogen atom, an alkyl group, an aryl group, an acyl group, an alkoxycarbonyl group, an aryloxycarbonyl group, or a carbamoyl group.

2. The chroman derivative according to claim 1, wherein each of $Y^1$ and $Y^2$ represents a hydrogen atom.

3. A method of producing a compound represented by the following Formula (II), the method comprising a step of allowing a compound represented by the following Formula (Ia) to react with an amine compound represented by the following Formula (III) in the presence of a solvent:

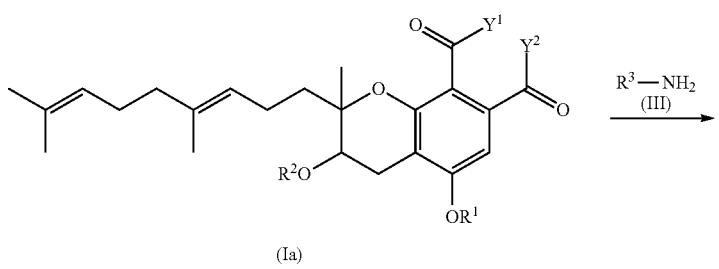

(Ia)

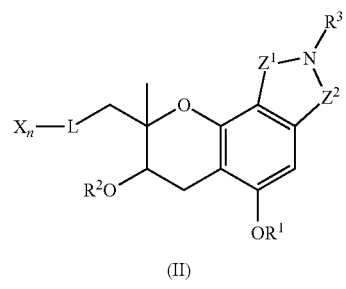

(II)

wherein, in the formulae, each of Y1 and Y2 independently represents a hydrogen atom; each of R1 and R2 independently represents a hydrogen atom, an alkyl group, an aryl group, an acyl group, an alkoxycarbonyl group, an aryloxycarbonyl group, or a carbamoyl group; Xn-L- represents a group represented by the following Formula (L0):

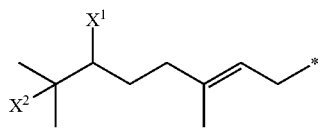

wherein, in the Formula (L0), $X^1$ and $X^2$ are linked to each other to form a single bond, and * indicates a linking position;

$Z^1$ represents a methylene group, and $Z^2$ represents a carbonyl group; and $R^3$ represents a hydrogen atom, an alkyl group, an aryl group, or a heterocyclic group.

4. The chroman derivative according to claim 1, wherein at least one of $Y^1$ or $Y^2$ represents a hydroxy group, an alkoxy group, an aryloxy group, or a halogen atom.

5. The chroman derivative according to claim 1, wherein at least one of $Y^1$ or $Y^2$ represents a hydroxy group, an alkoxy group having from 1 to 12 carbon atoms, an aryloxy group having from 6 to 14 carbon atoms, or a halogen atom.

6. The chroman derivative according to claim 1, wherein at least one of $Y^1$ or $Y^2$ represents a hydroxy group, an alkoxy group selected from the group consisting of methoxy group, an ethoxy group, a propoxy group, an isopropoxy group, a butoxy group, a t-butoxy group, a pentyloxy group, a hexyloxy group, a cyclohexyloxy group, an octyloxy group, an ethylhexyloxy group, a decyloxy group, and a dodecyloxy group, a phenyloxy group, or a halogen atom.

7. The chroman derivative according to claim 1, wherein each of $R^1$ and $R^2$ independently represents a hydrogen atom, an alkyl group having from 1 to 12 carbon atoms, an aryl group having from 6 to 14 carbon atoms, an alkylcarbonyl group having an alkyl group having from 1 to 12 carbon atoms, an arylcarbonyl group having an aryl group having from 6 to 14 carbon atoms, an alkoxycarbonyl group selected from the group consisting of a methoxycarbonyl group, an ethoxycarbonyl group, a propyloxycarbonyl group, and a t-butyloxycarbonyl group, a phenoxycarbonyl group, or a carbamoyl group.

8. The chroman derivative according to claim 1, wherein each of $R^1$ and $R^2$ independently represents a hydrogen atom, an alkyl group selected from the group consisting of a methyl group, an ethyl group, a propyl group, an isopropyl group, a butyl group, a t-butyl group, a pentyl group, a hexyl group, a cyclohexyl group, an octyl group, an ethylhexyl group, a decyl group, and a dodecyl group, an aryl group selected from the group consisting of a phenyl group, a naphthyl group, and an anthracenyl group, an alkylcarbonyl group having an alkyl group having from 1 to 4 carbon atoms, a phenylcarbonyl group, an alkoxycarbonyl group selected from the group consisting of a methoxycarbonyl group, an ethoxycarbonyl group, a propyloxycarbonyl group, and a t-butyloxycarbonyl group, a phenoxycarbonyl group, or a carbamoyl group.

9. The method according to claim 3, wherein each of $R^1$ and $R^2$ independently represents a hydrogen atom, an alkyl group having from 1 to 12 carbon atoms, an aryl group having from 6 to 14 carbon atoms, an alkylcarbonyl group having an alkyl group having from 1 to 12 carbon atoms, an arylcarbonyl group having an aryl group having from 6 to 14 carbon atoms, an alkoxycarbonyl group selected from the group consisting of a methoxycarbonyl group, an ethoxycarbonyl group, a propyloxycarbonyl group, and a t-butyloxycarbonyl group, a phenoxycarbonyl group, or a carbamoyl group.

10. The method according to claim 3, wherein each of $R^1$ and $R^2$ independently represents a hydrogen atom, an alkyl group selected from the group consisting of a methyl group, an ethyl group, a propyl group, an isopropyl group, a butyl group, a t-butyl group, a pentyl group, a hexyl group, a cyclohexyl group, an octyl group, an ethylhexyl group, a decyl group, and a dodecyl group, an aryl group selected from the group consisting of a phenyl group, a naphthyl group, and an anthracenyl group, an alkylcarbonyl group having an alkyl group having from 1 to 4 carbon atoms, a phenylcarbonyl group, an alkoxycarbonyl group selected from the group consisting of a methoxycarbonyl group, an ethoxycarbonyl group, a propyloxycarbonyl group, and a t-butyloxycarbonyl group, a phenoxycarbonyl group, or a carbamoyl group.

* * * * *